United States Patent [19]
Dory

[11] Patent Number: 5,143,074
[45] Date of Patent: Sep. 1, 1992

[54] ULTRASONIC TREATMENT DEVICE USING A FOCUSSING AND OSCILLATING PIEZOELECTRIC ELEMENT

[75] Inventor: Jacques Dory, Coupvray, France

[73] Assignee: EDAP International, France

[21] Appl. No.: 696,992

[22] Filed: May 3, 1991

Related U.S. Application Data

[60] Continuation of Ser. No. 427,429, Oct. 27, 1989, abandoned, which is a continuation-in-part of Ser. No. 368,906, Jun. 19, 1989, Pat. No. 5,080,101, which is a continuation of Ser. No. 37,369, Apr. 13, 1987, abandoned, which is a division of Ser. No. 728,905, Apr. 30, 1985, Pat. No. 4,658,828, which is a continuation-in-part of Ser. No. 674,889, Nov. 26, 1984, Pat. No. 4,617,931.

[30] Foreign Application Priority Data

Oct. 27, 1988 [FR] France .................. 88 14015

[51] Int. Cl.⁵ .......................... A61B 8/00; A61N 5/00
[52] U.S. Cl. .......................... 128/660.03; 128/24 AA; 128/399
[58] Field of Search ........ 128/660.03, 24 AA, 24 EL, 128/399, 804

[56] References Cited

U.S. PATENT DOCUMENTS 4,526,168 7/1985 Hassler et al. .................. 128/24 EL
4,771,787 9/1988 Wurster et al. .................. 128/660.03

FOREIGN PATENT DOCUMENTS 2187840 9/1987 United Kingdom ........... 128/660.03

Primary Examiner—Lee S. Cohen
Attorney, Agent, or Firm—William A. Drucker

[57] ABSTRACT

An ultrasonic treatment device is divulged comprising a power transducer in the form of a spherical cup serving both as treatment wave generator and as echographic transceiver, wherein the transducer is caused to oscillate (motor 2) during the treatment, so as to obtain sectorial B type scanning and it is excited (circuits 1 to 14) with treatment waves only in a restricted angular scanning sector and with echographic waves in the rest of the scanned sector.

7 Claims, 2 Drawing Sheets

ULTRASONIC TREATMENT DEVICE USING A FOCUSSING AND OSCILLATING PIEZOELECTRIC ELEMENT

CROSS REFERENCE TO PRIOR APPLICATIONS

This application is a continuation of Ser. No. 07/427,429, filed Oct. 27, 1989, now abandoned, which is a continuation-in-part of Ser. No. 07/368,906, filed Jun. 19, 1989, now U.S. Pat. No. 5,080,101, which is a continuation of Ser. No. 07/037,369, filed Apr. 13, 1987, now abandoned, which is a division of Ser. No. 06/728,905, filed Apr. 30, 1985, U.S. Pat. No. 4,658,828, now U.S. Pat. No. Re. 33,590 of May 21, 1991, which is a continuation-in-part of Ser. No. 06/674,889, filed Nov. 26, 1984, now U.S. Pat. No. 4,617,931 now Re-Examination Certificate B1-4,617,931 of Jul. 12, 1988.

BACKGROUND OF THE INVENTION

1. Field of the Invention

The invention relates to the treatment by an ultrasonic focussed beam of anatomical anomalies and, more particularly, of shallow structures for which the focal spot of the beam must be relatively fine.

2. Description of the Prior Art

The French patent 84 06877 describes a hyperthermia device using a power transducer in the form of a spherical cup which generates ultrasonic wave trains, having for example frequencies of the order of 500 kHz. The location of the anatomical target and observation thereof during firing takes place by means of an auxiliary transducer mechanically coupled to the cup and excited by an echographic pulse generator having, for example, a frequency of 5 MHz.

This device is adapted for the treatment of deep tissues, the 500 KHz frequency waves being relatively little absorbed during their propagation through the tissues. Considering its size (diameter of 200 to 300 mm for example) the cup is not capable of being subjected to rapid movement which would permit echographic scanning in real time and, in any case, its operating frequency would not be adapted to the formation of good quality echographic images.

The published Japanese patent application 58 188431 has in particular proposed using the power transducer alternately for the treatment and for the echography. When such a principle is used with a fixed power transducer, either a type A echography is carried out, which only delivers indications of the distance of the target or else scanning by the echographic beam is generated by excitation of the transducer with waves which are phase-shifted with respect to each other. This latter solution is complicated and does not provide scanning of the target in a sufficient angle. Furthermore, this principle does not make it possible to observe the target during the treatment sequence.

SUMMARY OF THE INVENTION

The invention proposes causing the power transducer to oscillate mechanically during treatment, at an oscillation speed and amplitude adapted for obtaining real time echographic scanning of the target, advantageously sectorial B type scanning, and in a predetermined restricted angular sector exciting said transducer with treatment waves (at least during certain scanning periods) whereas, during at least a part of the rest of the scanned sector, it will be excited with echographic pulses.

Thus, considering the relatively short duration of each firing interval with respect to the oscillation period, the mean power will be sufficient in certain treatments. The invention applies mainly to the treatment of structures only a few centimeters under the skin, for example ocular structures or blood vessels. In such applications, treatment waves are generally used at frequencies of the order of 5 to 10 MHz, which produce the very fine focal spots required. Although absorption of these waves in the tissues is very high, the mean power required remains of the order of 1 kW, because of the small propagation distance and because heating of the tissues is appreciable.

Since the power transducer may then have a relatively small diameter, for example of the order of 70 mm, it can be driven in oscillation by means of an electric motor.

BRIEF DESCRIPTION OF THE DRAWINGS

Other features and advantages of the invention will be clear from the following description.

In the accompanying drawings.

DESCRIPTION OF THE PREFERRED EMBODIMENT

Figure 1:
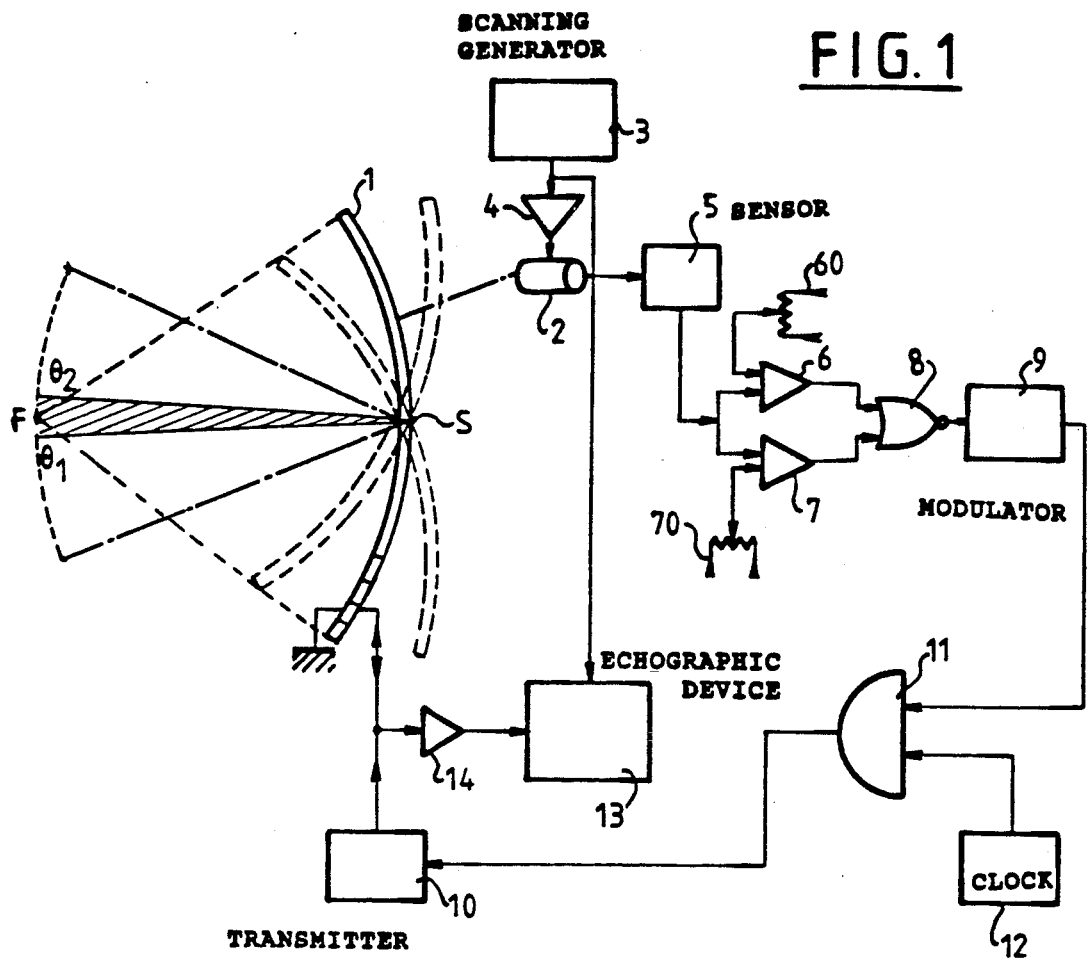
FIG. 1 shows schematically a treatment device according to a preferred embodiment of the invention.

In FIG. 1, a spherical cup 1 has been shown made from a piezoelectric ceramic and mounted for oscillating preferably about an axis tangential to the cup at the top S thereof. The angular amplitude of oscillation will, by way of example, be between 30° and 60°. The limits of the plane sector thus scanned by the axis SF of the cup have been shown with chain-dotted lines and the beam focussed at F transmitted by the cup in its median position with broken lines.

The oscillating movement of the cup is, as is known, obtained by means of an electric motor 2 controlled by a scanning generator 3 through an amplifier 4. An angular position sensor 5, of a type known per se, delivers an electric signal of variable amplitude as a linear function of the angle $\theta$ which axis SF forms with its median reference position.

By way of example, such a sensor may comprise a permanent magnet fast with the shaft of the motor and cooperating with a magnetic field sensor.

The signal indicative of $\theta$ is applied to two operational amplifiers 6 and 7 which further receive two reference signals indicative of two particular values of $\theta$, namely $\theta_1$ and $\theta_2$. These reference signals are adjustable by means of potentiometers 60 and 70 respectively.

The outputs of amplifiers 6 and 7, which are respectively at level 1 when $\theta \geq \theta_1$ and $\theta \geq \theta_2$ are connected to the inputs of a NAND gate 8 which controls a modulator 9. The output of modulator 9 is connected to the control input of a transmitter 10 through an OR gate 11, which further receives synchronization signals delivered by a clock 12. The transmitter 10 drives cup 1.

The latter has for example a diameter of 70 mm and is formed, in a way known per se, of a plurality of piezoelectric elements isolated from each other and juxtaposed so as to form a mosaic.

Transmitter 10 may in actual fact comprise several transmitting devices each exciting a group of elements of the cup. Since this technique is known, for clearness of the description it will be considered that the transmitter 10 only generates a single signal comprising, as will be explained hereafter, both power position trains intended for the treatment and echographic pulses. For these two types of transmission, the carrier frequency will advantageously be the same, for example 5 MHz.

The cup serves both as transducer transmitting the power pulses and the echographic pulses and as transducer receiving the echos formed by the reflection of the echographic pulses from the target.

The echos received are transmitted to an echographic device 13 of known type through an amplifier 14.

Figure 2:
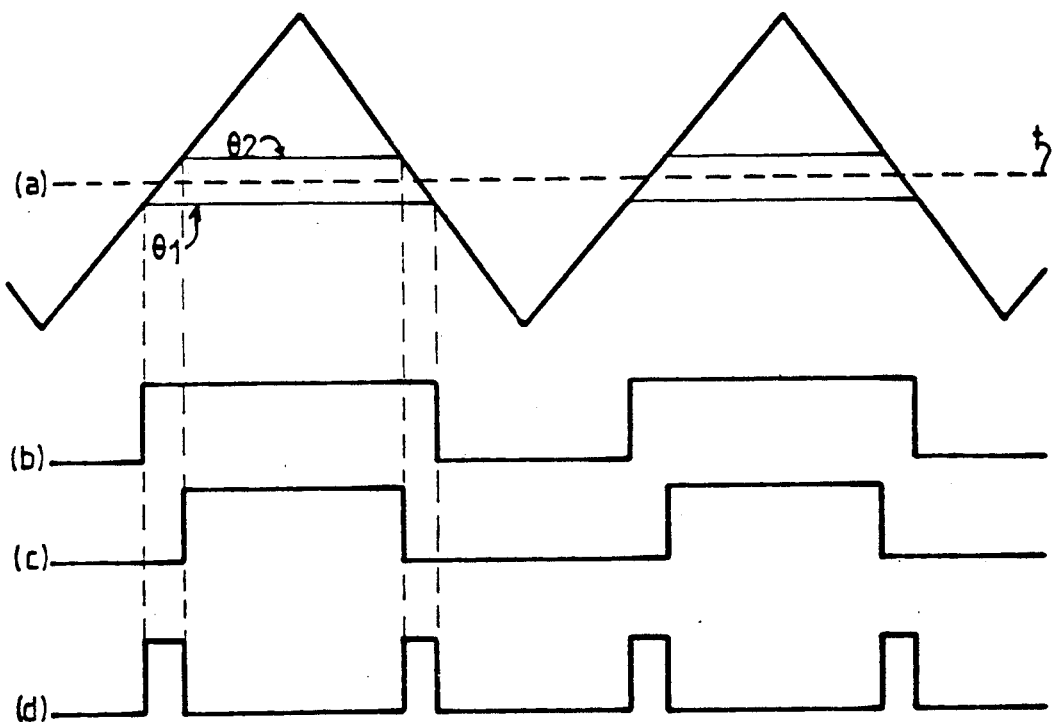
FIG. 2 illustrates the corresponding waveforms.

FIG. 2 shows at (a) the saw tooth signal generated by the scanning generator 3. By way of example, this signal has a period of 1/5 sec. so that the oscillation frequency of the cup is 5 Hz.

At (b) has been shown the output signal of amplifier 6, which is at level 1 when $\theta \geq \theta_1$, and at (c), the output signal of amplifier 7, which is at level 1 when $\theta \geq \theta_2$. The signal (d) at the output of gate 8 thus comprises a square wave at logic level 1 when $\theta_1 \leq \theta \leq \theta_2$, namely twice per period. In the intervals between these square waves (d), gate 11 transmits to transmitter 10 the pulses from clock 12 which have for example a high frequency of 5 MHz, so a duration of 0.2 microsecond, and a recurrence frequency of 10 kHz. These values are appropriate to the formation of a good quality echographic image with a scanning frequency of 5 Hz. During the echographic transmission, the transmitter 10 may be caused to work at reduced power, for example by reducing its supply voltage.

During each square wave (d) which will for example be of the order of 20 milliseconds, transmitter 10 generates treatment waves at the high frequency of 5 MHz.

The values of $\theta_1$ and $\theta_2$ are adjusted so that the target is situated in the firing angle.

After initial location of the target effected by moving the oscillating cup in space until a mark materializing, on the screen of the echographic device, the theoretical position of its focal point F is made to coincide with the echographic image of the zone to be treated, obtained as has just been mentioned, $\theta_1$ and $\theta_2$ may be adjusted for aiming at a precise target in the zone to be treated. Should the target move during treatment or if it is noted that firing is not correctly aimed, it is sufficient to readjust the setting by a small movement of the oscillating cup.

Figure 3:
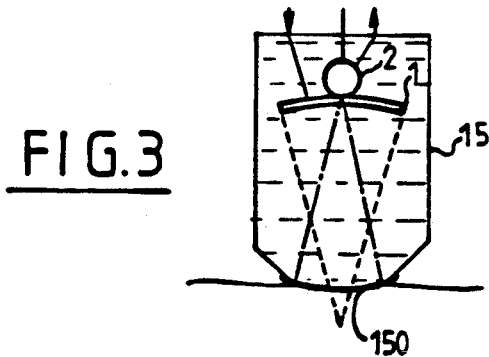
FIG. 3 shows the transducer assembly.

FIG. 3 shows that the oscillating cup 1 and the motor 2 which drives it in oscillation are immersed in a coupling liquid contained in a case 15 whose front face is provided with a deformable membrane 150 which is transparent to ultra-sounds. This membrane has a sufficient area for transmitting the echographic scanning cone and is brought in contact with the skin of the patient.

Depending on the depth of the tumour, the treatment waves will be transmitted inside each square wave by discontinuous trains, the transmission time for each train varying between a few tens and a few hundreds of microseconds. The peak transmission power, all the higher the shorter the train, may reach several hundred kW, the high peak powers and the short transmissions having the advantage of preventing thermal diffusion of the energy which would reduce the firing accuracy.

When the mean power desired for the treatment is high, the speed of the motor may be varied during each scanning cycle so as to slow down scanning during the transmission square waves of the treatment waves.

Instead of sectorial scanning, linear scanning may be used and, for this, a linear oscillating movement will be imparted to the transducer.

What is claimed is:

1. An ultrasonic device for treatment of an anatomical anomaly, said device comprising:
   (a) a power transducer in the form of a self-focussing cup associated with a power excitation generator generating power wave trains and with an echographic device transmitting an echographic beam and using said transducer as an echo receiver, said device further comprising:
   (b) means for causing said echographic device continuously to oscillate during the treatment, at an oscillation speed and with an amplitude adapted for obtaining real time echographic beam scanning of a region of space containing the anatomical anomaly, and
   (c) means for exciting said power transducer to produce treatment waves at moments when the echographic beam scans a predetermined restricted portion of said region.

2. The device as claimed in claim 1, wherein the scanning is sectorial type B scanning and said moments correspond to the passage of the beam in a predetermined restricted angular sector.

3. The device as claimed in claim 2, including an angular position sensor means providing output signals which define said restricted angular sector and a logic circuit coupled to said sensor means for deriving square wave signals controlling said power excitation generator.

4. The device as claimed in claim 3, wherein said power excitation generator further generates echographic pulses which are applied to said cup for transmitting said echographic beam.

5. The device as claimed in claim 1, wherein the means causing said echographic device to oscillate causes a linear oscillating movement.

6. In an ultrasonic treatment device comprising a power transducer in the form of a self-focussing cup associated with a power excitation generator and with an echographic device transmitting an echographic beam using said power transducer as an echo receiver, and further comprising means for causing said echographic device to oscillate during treatment at an oscillation speed and amplitude adapted for obtaining real time echographic scanning, the improvement comprising:
   (a) means for exciting said power transducer to produce a sequence of treatment waves at moments when the echographic beam scans a predetermined restricted region of a firing space; and
   (b) means for exciting said echographic device to produce echographic waves during intervals between said moments.

7. A device according to claim 6 including means by which said echographic waves are received by said power transducer in intervals between treatment waves and during an interrupted sequence of treatment waves.

* * * * *